(12) United States Patent
Cho et al.

(10) Patent No.: US 8,388,976 B2
(45) Date of Patent: Mar. 5, 2013

(54) POLYPEPTIDE SPECIFICALLY BINDING TO VASCULAR ENDOTHELIAL GROWTH FACTOR, FUSION PROTEIN INCLUDING POLYPEPTIDE, AND METHODS THEREFOR

(75) Inventors: A-yeon Cho, Seongnam-si (KR); Min-kyung Kim, Seoul (KR); Brian Hosung Min, Seongnam-si (KR); Jong-sang Ryu, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 13/588,715

(22) Filed: Aug. 17, 2012

(65) Prior Publication Data

US 2012/0316318 A1    Dec. 13, 2012

Related U.S. Application Data

(62) Division of application No. 12/973,488, filed on Dec. 20, 2010, now Pat. No. 8,268,322.

(30) Foreign Application Priority Data

Dec. 22, 2009 (KR) .................. 10-2009-0129135

(51) Int. Cl.
| | | |
|---|---|---|
| A61K 39/00 | (2006.01) | |
| A61K 39/38 | (2006.01) | |
| A61K 39/395 | (2006.01) | |
| A61K 45/00 | (2006.01) | |
| A61K 47/00 | (2006.01) | |
| A61B 5/055 | (2006.01) | |

(52) U.S. Cl. ............... 424/185.1; 424/9.34; 424/130.1; 424/134.1; 424/143.1; 424/178.1; 424/184.1; 424/192.1; 424/194.1; 424/278.1; 435/68.1; 435/69.1; 435/69.3; 514/8.1

(58) Field of Classification Search ............... None
See application file for complete search history.

*Primary Examiner* — Ja'na Hines
(74) *Attorney, Agent, or Firm* — Leydig, Voit & Mayer, Ltd.

(57) ABSTRACT

A polypeptide inhibiting binding between a vascular endothelial growth factor and a vascular endothelial growth factor receptor, a fusion protein including the same, and a method of preparing the fusion protein are disclosed.

6 Claims, 5 Drawing Sheets

FIG. 2
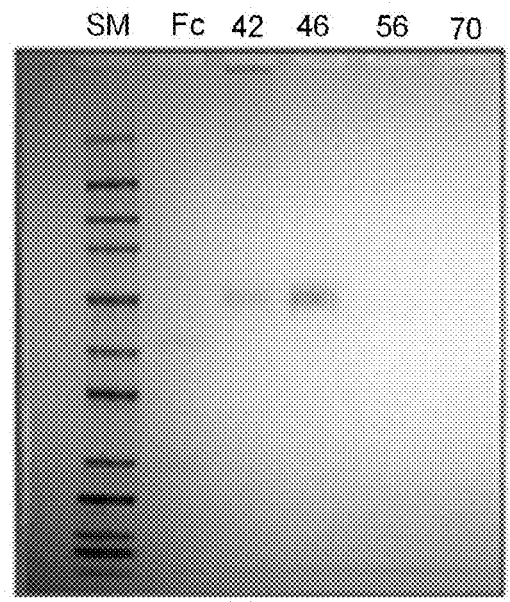 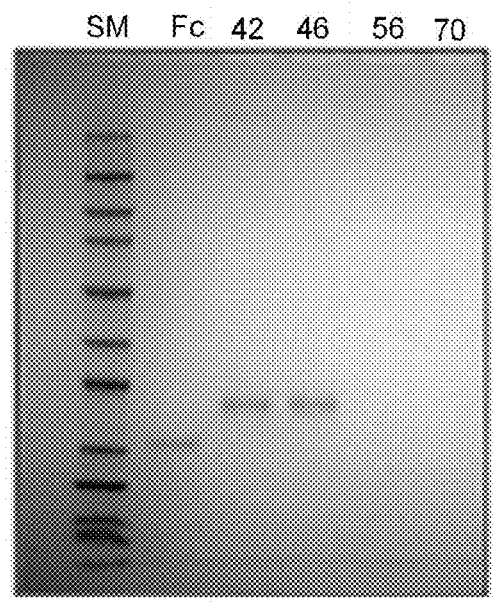

SEQUENCE LISTING

```
<160> NUMBER OF SEQ ID NOS: 51

<210> SEQ ID NO 1
<211> LENGTH: 10
<212> TYPE: PRT
<213> ORGANISM: Artificial Sequence
<220> FEATURE:
<223> OTHER INFORMATION: polypeptide binding specifically to VEGFR-2

<400> SEQUENCE: 1

Pro Arg Phe Glu Met Trp His Asp Asp Lys
```

```
                        1               5                   10
```

<210> SEQ ID NO 2
<211> LENGTH: 10
<212> TYPE: PRT
<213> ORGANISM: Artificial Sequence
<220> FEATURE:
<223> OTHER INFORMATION: polypeptide binding specifically to VEGFR-2

<400> SEQUENCE: 2

```
Pro Arg Leu Ser Met Trp Gln Asn Met Glu
 1               5                   10
```

<210> SEQ ID NO 3
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 3

```
Asp Arg Phe Ser Met Trp Lys Asn Leu Glu
 1               5                   10
```

<210> SEQ ID NO 4
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 4

```
Ser Arg Phe Glu Met Trp Asn Asp Ile Ser
 1               5                   10
```

<210> SEQ ID NO 5
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 5

```
Asp Arg Phe Thr Met Trp Asp Ser Gln Ser
 1               5                   10
```

<210> SEQ ID NO 6
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 6

```
Gln Arg Asp Gln Gln Tyr Lys His Met Tyr
 1               5                   10
```

<210> SEQ ID NO 7
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 7

```
Asp Arg Tyr Ser Gln Tyr Gln Ser Pro Met
 1               5                   10
```

```
<210> SEQ ID NO 8
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 8

Asp Phe Leu Lys Met Tyr Arg Asp Glu Lys
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 9

Met His Arg Pro Trp Pro Trp Asp Met Phe
 1               5                  10

<210> SEQ ID NO 10
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 10

Gln Met Asp Arg Met Phe Pro His Val Gly
 1               5                  10

<210> SEQ ID NO 11
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 11

Pro Ile Gly Gln Arg Trp Asn Arg Leu Glu
 1               5                  10

<210> SEQ ID NO 12
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 12

Arg Leu Phe Glu Met Tyr Pro Ser Leu Glu
 1               5                  10

<210> SEQ ID NO 13
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 13

Glu Arg Thr Glu Met Phe Pro Ser Ala Ser
 1               5                  10

<210> SEQ ID NO 14
```

```
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 14

Gln Arg Asp Glu Met Tyr Pro His Leu Asn
 1               5                  10

<210> SEQ ID NO 15
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 15

Pro His Gln Glu Met Trp Gln Phe Glu Ser
 1               5                  10

<210> SEQ ID NO 16
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 16

Met Lys Ser Ala Met Tyr His Asp Ile Arg
 1               5                  10

<210> SEQ ID NO 17
<211> LENGTH: 10
<212> TYPE: PRT
<213> ORGANISM: Artificial Sequence
<220> FEATURE:
<223> OTHER INFORMATION: polypeptide binding specifically to VEGF

<400> SEQUENCE: 17

Phe Asp Lys Tyr Tyr Arg Asp Trp Phe Ile
 1               5                  10

<210> SEQ ID NO 18
<211> LENGTH: 9
<212> TYPE: PRT
<213> ORGANISM: Artificial Sequence
<220> FEATURE:
<223> OTHER INFORMATION: polypeptide binding specifically to VEGF

<400> SEQUENCE: 18

Arg Met Gly Pro Phe Gly Thr Thr His
 1               5

<210> SEQ ID NO 19
<211> LENGTH: 9
<212> TYPE: PRT
<213> ORGANISM: Artificial Sequence
<220> FEATURE:
<223> OTHER INFORMATION: polypeptide binding specifically to VEGF

<400> SEQUENCE: 19

Tyr Arg Gly Val Trp Gly Gly Tyr Phe
 1               5

<210> SEQ ID NO 20
<211> LENGTH: 9
<212> TYPE: PRT
```

```
<213> ORGANISM: Artificial Sequence
<220> FEATURE:
<223> OTHER INFORMATION: polypeptide binding specifically to VEGF

<400> SEQUENCE: 20

His Asp Tyr Ala Phe Tyr Ser Ala Trp
 1               5

<210> SEQ ID NO 21
<211> LENGTH: 9
<212> TYPE: PRT
<213> ORGANISM: Artificial Sequence
<220> FEATURE:
<223> OTHER INFORMATION: polypeptide binding specifically to VEGF

<400> SEQUENCE: 21

Glu Asp Tyr Arg Phe Tyr Ser Val Trp
 1               5

<210> SEQ ID NO 22
<211> LENGTH: 9
<212> TYPE: PRT
<213> ORGANISM: Artificial Sequence
<220> FEATURE:
<223> OTHER INFORMATION: polypeptide binding specifically to VEGF

<400> SEQUENCE: 22

Thr Trp Trp Thr His Asp Phe Thr Ile
 1               5

<210> SEQ ID NO 23
<211> LENGTH: 8
<212> TYPE: PRT
<213> ORGANISM: Artificial Sequence
<220> FEATURE:
<223> OTHER INFORMATION: polypeptide binding specifically to VEGF

<400> SEQUENCE: 23

Tyr Gly Tyr Pro Trp Ser Gly Thr
 1               5

<210> SEQ ID NO 24
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 24
cctcgttttg agatgtggca tgatgataag                                    30

<210> SEQ ID NO 25
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 25
cctcgtcttt ctatgtggca gaatatggag                                    30

<210> SEQ ID NO 26
<211> LENGTH: 30
<212> TYPE: DNA
<213> ORGANISM: Artificial Sequence
<220> FEATURE:
```

<223> OTHER INFORMATION: polynucleotide encoding polypeptide binding
      specifically to VEGF

<400> SEQUENCE: 26
gatcgttttt ctatgtggaa gaatcttgag                                              30

<210> SEQ ID NO 27
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 27
tctcgttttg agatgtggaa tgatatttct                                              30

<210> SEQ ID NO 28
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 28
aatcgtctta ttatgcatac ttctgagcag                                              30

<210> SEQ ID NO 29
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 29
cagcgtgatc agcagtataa gcatatgtat                                              30

<210> SEQ ID NO 30
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 30
gatcgttatt ctcagtatca gtctcctatg                                              30

<210> SEQ ID NO 31
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 31
gattttctta agatgtatcg tgatgagaag                                              30

<210> SEQ ID NO 32
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

```
<400> SEQUENCE: 32
atgcatcgtc cttggccttg ggatatgttt                                    30

<210> SEQ ID NO 33
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 33
cagatggatc gtatgtttcc tcatgttggt                                    30

<210> SEQ ID NO 34
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 34
cctattggtc agcgttggaa tcgtcttgag                                    30

<210> SEQ ID NO 35
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 35
cgtctttttg agatgtatcc ttctcttgag                                    30

<210> SEQ ID NO 36
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 36
gagcgtactg agatgtttcc ttctgcttct                                    30

<210> SEQ ID NO 37
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 37
cagcgtgatg agatgtatcc tcatcttaat                                    30

<210> SEQ ID NO 38
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 38
```
cctcatcagg agatgtggca gtttgagtct                                        30

<210> SEQ ID NO 39
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 39
atgaagtctg ctatgtatca tgatattcgt                                        30

<210> SEQ ID NO 40
<211> LENGTH: 30
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 40
tttgataagt attatcgtga ttggtttatt                                        30

<210> SEQ ID NO 41
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 41
cgtatgggtc cttttggtac tactcat                                           27

<210> SEQ ID NO 42
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 42
tatcgtggtg tttggggtgg ttattttt                                          27

<210> SEQ ID NO 43
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 43
catgattatg cttttattc tgcttgg                                            27

<210> SEQ ID NO 44
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 44
gaggattatc gttttattc tgtttgg                                            27

<210> SEQ ID NO 45
<211> LENGTH: 27
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 45
actcgtcttc agattctttg gggtgtt                                          27

<210> SEQ ID NO 46
<211> LENGTH: 24
<212> TYPE: DNA
<213> ORGANISM: Artificial Sequence
<220> FEATURE:
<223> OTHER INFORMATION: polynucleotide encoding polypeptide binding
      specifically to VEGF

<400> SEQUENCE: 46
tatggttatc cttggtctgg tact                                             24

<210> SEQ ID NO 47
<211> LENGTH: 27
<212> TYPE: DNA
<213> ORGANISM: Artificial Sequence
<220> FEATURE:
<223> OTHER INFORMATION: TN8,9-forward primer

<400> SEQUENCE: 47
ggaggaagcg gccgcsgymc yggyrry                                          27

<210> SEQ ID NO 48
<211> LENGTH: 26
<212> TYPE: DNA
<213> ORGANISM: Artificial Sequence
<220> FEATURE:
<223> OTHER INFORMATION: TN7,8,9-reverse primer
<220> FEATURE:
<221> NAME/KEY: misc_difference
<222> LOCATION: (15)
<223> OTHER INFORMATION: "n" represents any of nucleotide A, G, T or C
<220> FEATURE:
<221> NAME/KEY: misc_difference
<222> LOCATION: (24)
<223> OTHER INFORMATION: "n" represents any of nucleotide A, G, T or C

<400> SEQUENCE: 48
cctcctctct agagnggytc mgtncc                                           26

<210> SEQ ID NO 49
<211> LENGTH: 27
<212> TYPE: DNA
<213> ORGANISM: Artificial Sequence
<220> FEATURE:
<223> OTHER INFORMATION: TN10-forward primer

<400> SEQUENCE: 49
ggaggaagcg gccgcggtac tggcagt                                          27

<210> SEQ ID NO 50
<211> LENGTH: 26
<212> TYPE: DNA
<213> ORGANISM: Artificial Sequence
<220> FEATURE:
<223> OTHER INFORMATION: TN10-reverse primer

<400> SEQUENCE: 50

```
cctcctctct agagaggacc cggggc                                               26

<210> SEQ ID NO 51
<211> LENGTH: 10
<212> TYPE: PRT
<213> ORGANISM: Artificial Sequence
<220> FEATURE:
<223> OTHER INFORMATION: isolated polypeptide inhibiting binding between
      a vascular endothelial growth factor and a vascular endothelial
      growth factor receptor
<220> FEATURE:
<221> NAME/KEY: PEPTIDE
<222> LOCATION: (1)
<223> OTHER INFORMATION: an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys
<220> FEATURE:
<221> NAME/KEY: PEPTIDE
<222> LOCATION: (3)
<223> OTHER INFORMATION: an amino acid selected from the group
      consisting of Ala, Ile, Leu, Met, Phe, Pro, Trp, and Val
<220> FEATURE:
<221> NAME/KEY: PEPTIDE
<222> LOCATION: (4)
<223> OTHER INFORMATION: an amino acid selected from the group
      consisting of Asn, Cys, Gln, Gly, Ser, Thr, Tyr, Asp, and Glu
<220> FEATURE:
<221> NAME/KEY: PEPTIDE
<222> LOCATION: (7)
<223> OTHER INFORMATION: an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys
<220> FEATURE:
<221> NAME/KEY: PEPTIDE
<222> LOCATION: (8)
<223> OTHER INFORMATION: an amino acid selected from the group
      consisting of Asn, Cys, Gln, Gly, Ser, Thr, Tyr, Asp, and Glu
<220> FEATURE:
<221> NAME/KEY: PEPTIDE
<222> LOCATION: (9)
<223> OTHER INFORMATION: an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys
<220> FEATURE:
<221> NAME/KEY: PEPTIDE
<222> LOCATION: (10)
<223> OTHER INFORMATION: an amino acid selected from the group
      consisting of Ala, Ile, Leu, Met, Phe, Pro, Trp, Val, Asn, Cys,
      Gln, Gly, Ser, Thr, Tyr, Asp, Glu, Arg, His, and Lys

<400> SEQUENCE: 51

Xaa Arg Xaa Xaa Met Trp Xaa Xaa Xaa Xaa
 1               5                  10
```

POLYPEPTIDE SPECIFICALLY BINDING TO VASCULAR ENDOTHELIAL GROWTH FACTOR, FUSION PROTEIN INCLUDING POLYPEPTIDE, AND METHODS THEREFOR

CROSS-REFERENCE TO RELATED APPLICATIONS

This application claims priority to U.S. patent application Ser. No. 12/973,488, filed Dec. 20, 2010, which claims priority to Korean Patent Application No. 10-2009-0129135, filed on Dec. 22, 2009, and all the benefits accruing therefrom under 35 U.S.C. §119, the content of which in its entirety is herein is incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 14,354 Byte ASCII (Text) file named "710875_ST25.txt," created on Aug. 17, 2012.

BACKGROUND

1. Field

The present disclosure related to polypeptides inhibiting binding between a vascular endothelial growth factor and a vascular endothelial growth factor receptor, fusion proteins including the inhibiting polypeptides, and methods of preparing the fusion proteins.

2. Description of the Related Art

Angiogenesis is a process involving the growth of new blood vessels from existing vessels, which plays a vital role in formation of organs, normal biological growth, and wound healing. In addition, abnormal angiogenesis is known to be an important contributor to diseases such as development and metastasis of tumor cells, age-related macular degeneration, diabetic retinopathy, psoriasis, rheumatoid arthritis, and chronic inflammation.

The development and metastasis of tumor cells depend on angiogenesis. Thus, since it has been suggested that a hypothesis in which anti-angiogenesis therapeutic drugs would become novel anti-cancer therapeutic drugs, research into the mechanism of angiogenesis has been conducted to develop a new anti-cancer therapeutic drug. Among various angiogenesis factors, research into the function of vascular endothelial growth factor (VEGF) has been conducted most actively. When tumor tissues develop, the tumor tissues cause vessel regression and the tumor tissues are excessively grown to form a hypoxic environment therein. As a result, conditions where angiogenesis occurs are provided within the tumor tissue. Under the conditions, vascular endothelial cells increase expression of VEGF to form new vessels around tumor cells. Since the growth of the vascular endothelial cells and vascular formation are induced by expression of VEGF and reaction between VEGF and vascular endothelial growth factor receptor (VEGFR), the reactions described above are a vital process in angiogenesis. Thus, angiogenesis in tumor tissues is suppressed by inhibiting binding between VEGF and VEGFR, and a compound that inhibits binding between VEGF and VEGFR may become an anti-cancer drug candidate or provide a target for developing anti-cancer therapies. In addition, VEGF may emerge as effective target for anti-cancer therapy in that VEGF is a ligand initiating transduction by VEGFR of intracellular signals for vascular formation.

A humanized antibody binding to human VEGF is approved for treating colon cancer and rectal cancer. However, targeting VEGF using currently available therapies is not effective for all patients or other kinds of cancers.

SUMMARY

Provided are polypeptides inhibiting binding between a vascular endothelial growth factor (VEGF) and a vascular endothelial growth factor receptor (VEGFR).

Provided are fusion proteins including a polypeptide inhibiting binding between a VEGF and a VEGFR and an Fc region of an antibody.

Polynucleotides encoding the fusion proteins are also provided.

Provided are recombinant vectors including the polynucleotides encoding the fusion proteins and host cells expressing the fusion proteins.

Provided are methods of preparing the fusion protein including a polypeptide inhibiting binding between a VEGF and a VEGFR and an Fc region of an antibody. In an embodiment, the method includes culturing a host cell disclosed herein under conditions that allow expression of the fusion protein, and collecting the fusion protein expressed from the culture.

Methods of treating an angiogenesis-related disease or cancer in a subject are also provided. In an embodiment, the method includes administering to a subject having an angiogenesis-related disease or cancer a therapeutically effective amount of a fusion protein disclosed here.

BRIEF DESCRIPTION OF THE DRAWINGS

These and/or other aspects of the present invention will become apparent and more readily appreciated from the following description of the embodiments, taken in conjunction with the accompanying drawings of which:

FIG. 2 presents images of non-denatured polyacrylamide gel electrophoresis (PAGE) results and denatured SDS PAGE results of a polypeptide according to an embodiment of the present invention and a human Fc fusion protein (lane labels 42, 46, 56, 70 refer to the polypeptide clone number);

DETAILED DESCRIPTION

Figure 1:
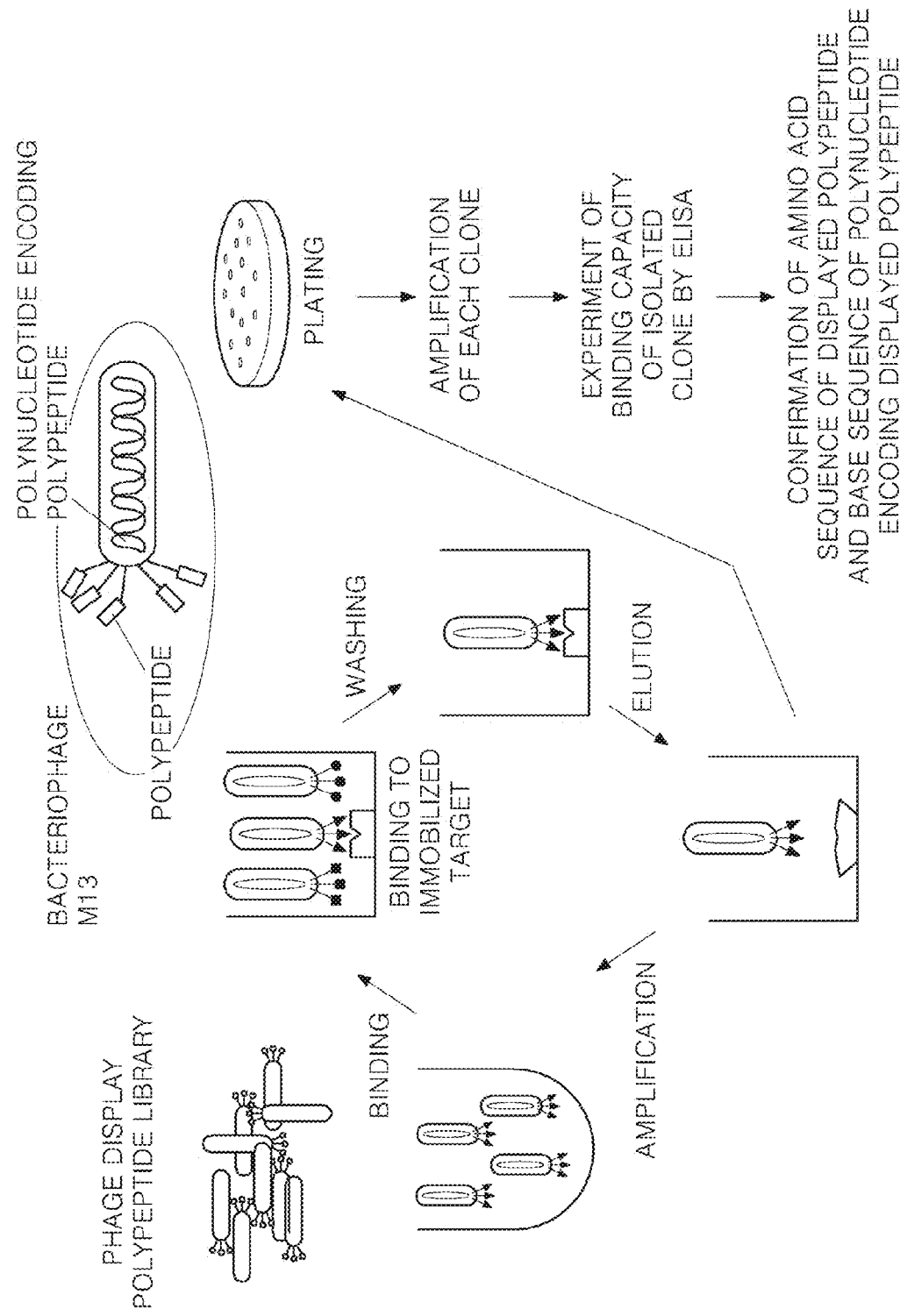
FIG. 1 is a schematic flowchart illustrating a process of screening for a polypeptide inhibiting binding between a vascular endothelial growth factor and a vascular endothelial growth factor receptor according to an embodiment of the present invention.

Reference will now be made in detail to embodiments of the invention, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

According to an embodiment of the present invention, there is provided a polypeptide that has an amino acid sequence represented by Formula I below, and inhibits binding between a vascular endothelial growth factor (VEGF) and a vascular endothelial growth factor receptor (VEGFR):

$X_1$-Arg-$X_2$-$X_3$-Met-Trp-$X_4$-$X_5$-$X_6$-$X_7$ (SEQ ID NO: 51) <Formula I> wherein $X_1$, $X_4$, $X_6$, and $X_7$ are each independently an amino acid selected from the group consisting of Ala, Ile, Leu, Met, Phe, Pro, Trp, Val, Asn, Cys, Gln, Gly, Ser, Thr, Try, Asp, Glu, Arg, His, and Lys, $X_2$ is an amino acid selected from the group consisting of Ala, Ile, Leu, Met, Phe, Pro, Trp, and Val, and $X_3$ and $X_5$ are each independently an amino acid selected from the group consisting of Asn, Cys, Gln, Gly, Ser, Thr, Try, Asp, and Glu.

The polypeptide may have an amino acid sequence selected from the group consisting of SEQ ID NOS: 1 through 5.

According to an embodiment of the present invention, there is provided a polypeptide that has one amino acid sequence selected from the group consisting of SEQ ID NOS: 6 through 23 and inhibits binding between a vascular endothelial growth factor and a vascular endothelial growth factor receptor.

The term "vascular endothelial growth factor (VEGF)" used herein refers to a family of proteins involved in growing endothelial cells to create new blood vessels. A VEGF is secreted as a dimeric glycoprotein, and contains 8 cysteine residues. For example, the VEGF may be protein having amino acid sequences published in Genbank Accession No. AAL27630 or AAA35789.

The term "vascular endothelial growth factor receptor (VEGFR)" used herein refers to a type of receptor tyrosine kinase existing in cell membranes of vascular endothelial cells, which allows induction of angiogenesis by transducing signals into cells when a ligand, e.g., a vascular endothelial growth factor, binds to the VEGFR. There are three kinds of vascular endothelial growth factor receptors, such as VEGFR-1, VEGFR-2, and VEGFR-3. The VEGFR consists of 7 immunoglobulin-like domains, a single transmembrane domain, and an intracellular kinase domain. For example, the VEGFR may be a protein having an amino acid sequences published as GenBank Accession No. ACF47599.

The term "specifically binding" used herein is known to one of ordinary skill in the art, and indicates that interaction occurs between molecules of at least two polypeptides or proteins by a covalent bond or a non-covalent bond with a high affinity. For example, an antibody and an antigen specifically bind to each other to immunologically react with each other.

The term "polypeptide" used herein refers to a chain of amino acid residues linked together by peptide bonds. For example, the polypeptide may have 4-10 amino acid residues, but is not limited thereto. In some embodiments, "polypeptide" refers to inhibitor polypeptides disclosed herein which can also inhibit another polypeptide or protein.

A polypeptide may be prepared using one of various known methods in the art, such as a gene cloning method or solid-phase synthesis techniques. In addition, a polypeptide may be experimentally obtained from a commercially available polypeptide library (for example, polypeptide libraries manufactured by Dyax, bacteriophage M13-polypeptide library manufactured by New England Biolab, and the like).

In Formula I, Asn, Cys, Gln, Gly, Ser, Thr, and Try are polar amino acids with uncharged R groups, Asp, Glu, Arg, His, and Lys are amino acids with charged R groups, and Ala, Ile, Leu, Met, Phe, Pro, Trp, and Val are non-polar amino acids with R groups.

According to an embodiment of the present invention, there is provided a fusion protein including the polypeptide that has an amino acid sequence represented by Formula I and that inhibits binding between a VEGF and a VEGFR; and an Fc region of an antibody. That is, the fusion protein can retain the ability to inhibit binding between VEGFR and VEGF and also retain the antigen-recognition function of the Fc region. In an embodiment, the polypeptide that has an amino acid sequence represented by Formula I may have an amino acid sequence selected from the group consisting of SEQ ID NO:1 through SEQ ID NO: 5.

According to an embodiment of the present invention, there is provided a fusion protein including a polypeptide that has one amino acid sequence selected from the group consisting of SEQ ID NOS: 6 through 23 and that inhibits binding between a VEGF and a VEGFR; and an Fc region of an antibody.

The fusion protein may further include a linker that links the polypeptide to the Fc region of the antibody.

The fusion protein may also be referred to as a peptibody. The term "peptibody" used herein refers to molecules including at least one polypeptide directly or indirectly linked to an Fc region of an antibody. The polypeptide may specifically bind a target. For example, the polypeptide in the peptibody may be a polypeptide that inhibits binding between a VEGF and a VEGFR.

The term, "link", as used herein, shall mean the linking of two or more biomolecules so that the biological functions, activities, and/or structure associated with the biomolecules are at least retained. In reference to polypeptides, the term means that the linking of two or more polypeptides results in a fusion polypeptide that retains at least some of the respective individual activities of each polypeptide component. The two or more polypeptides may be linked directly or via a linker.

The fusion protein may include a linker, for example, a peptide linker. Various known linkers in the art may be used. The linker may be a peptide linker consisting of a plurality of amino acid residues. The peptide linker may allow the polypeptide that inhibits binding between VEGF and a VEGFR and the polypeptide consisting of an Fc region of an antibody to be spaced apart from each other by a sufficient distance so that each of the polypeptide domains is folded in its appropriate secondary and tertiary structures. For example, the peptide linker may include Gly, Asn and Ser residues, and may also include neutral amino acid residues, such as Thr and Ala. Amino acid sequences suitable for the peptide linker are well-known in the art. For example, the amino acid sequence may be (Gly$_4$-Ser)$_3$ or Gly$_4$-Ser-Gly$_5$-Ser. The linker may be unnecessary or have various lengths, as long as it does not affect the biological activity of the fusion protein. The polypeptide that inhibits binding between a VEGF and a VEGFR and the polypeptide consisting of an Fc region of an antibody may be consecutively linked together in the presence of the peptide linker.

In addition, the peptide linker may be linked to the N-terminus and/or C-terminus of the polypeptide. In particular, when a peptide linker is linked to both the N-terminal and C-terminal of the polypeptide, each peptide linker may include cysteine. For example, when the cysteines are respectively linked to the N-terminal and C-terminal of the polypeptide, a disulfide bond may be formed between the two cysteines so that the polypeptide may exist between them, which can form a circular polypeptide including the polypeptide that inhibits binding between VEGF and a VEGFR.

The Fc region of the antibody may be derived from an animal selected from the group consisting of a human, a mouse, a rabbit, and a goat.

In an embodiment, the inhibitor polypeptide or the fusion protein including the same may specifically bind a VEGF to inhibit binding between a VEGF and a VEGFR. For example, the inhibition of the binding between a VEGF and a VEGFR may be carried out in such a way that the inhibitor polypeptide or the fusion protein binds the VEGF to prevent the VEGF from binding to the VEGFR. The inhibition of the binding between a VEGF and a VEGFR may also be carried out in such a way that transduction of intracellular signals generated by the binding between a VEGF and a VEGFR is blocked, for example, angiogenesis signals.

According to an embodiment of the present invention, there is provided a polynucleotide encoding a fusion protein including the polypeptide that has an amino acid sequence represented by Formula I and inhibits binding between a VEGF and a VEGFR; and an Fc region of an antibody.

The polynucleotide may have a nucleotide sequence selected from the group consisting of SEQ ID NOS: 24 through 28.

According to an embodiment of the present invention, there is provided a polynucleotide encoding a fusion protein including a polypeptide that has one amino acid sequence selected from the group consisting of SEQ ID NOS: 6 through 23 and inhibits binding between a VEGF and a VEGFR; and an Fc region of an antibody.

The polynucleotide may have a nucleotide sequence selected from the group consisting of SEQ D NOS: 29 through 46.

The encoded fusion protein may further include a linker that links the polypeptide to the Fc region of the antibody.

The term "polynucleotide" used herein refers to a polymer of deoxyribonucleotide or ribonucleotide that exists in a single-stranded or double-stranded form. The polynucleotide includes RNA genome sequences, DNA (gDNA and cDNA), and RNA sequences transcribed therefrom, and includes analogues of natural polynucleotide, unless otherwise indicated.

The polynucleotide includes a nucleotide sequence encoding the amino acid sequence of the fusion protein or a nucleotide sequence complementary thereto. The complementary sequences include completely complementary sequences and substantially complementary sequences. For example, a complementary sequence indicates a sequence that may be hybridized with the nucleotide sequence encoding the amino acid sequence of the fusion protein under stringent conditions known in the art. Specifically, stringent conditions mean, for example, hybridization to DNA in 6×SSC at about 45° C., followed by one or more washes in 0.2×SSC/0.1% SDS at about 50° C.-65° C.

"Isolated," when used to describe the various polypeptides, fusion proteins, or polynucleotides disclosed herein, means a polypeptide, fusion protein, or polynucleotide that has been identified and separated and/or recovered from a component of its natural environment. The term also embraces recombinant polynucleotides and polypeptides and chemically synthesized polynucleotides and polypeptides.

According to an embodiment of the present invention, there is provided a recombinant vector including a polynucleotide encoding a fusion protein including the polypeptide that has an amino acid sequence represented by Formula I and that inhibits binding between a VEGF and a VEGFR; and an Fc region of an antibody, and a promoter operatively linked to the sequence of the polynucleotide.

According to an embodiment of the present invention, there is provided a recombinant vector including a polynucleotide encoding a fusion protein including a polypeptide that has one amino acid sequence selected from the group consisting of SEQ ID NOS: 6 through 23 and that inhibits binding between a VEGF and a VEGFR; and an Fc region of an antibody, and a promoter operatively linked to the sequence of the polynucleotide.

The encoded fusion protein may further include a linker that links the polypeptide to the Fc region of the antibody.

The term "vector" used herein refers to a polynucleotide for transporting a target nucleic acid sequence, e.g., a gene, into and expressing the target gene in a host cell. For example, the vector may be a plasmid vector, a cosmid vector, and a virus vector, such as a bacteriophage vector, an adenovirus vector, a retrovirus vector, or an adeno-associated virus vector. The recombinant vector may be prepared by manipulating a plasmid, such as pSC101, pGV1106, pACYC177, ColE1, pKT230, pME290, pBR322, pUC8/9, pUC6, pBD9, pHC79, pIJ61, pLAFR1, pHV14, pGEX series, pET series, and pUC19, a phage, such as λgt4λB, λ-Charon, λΔz1, and M13, or a virus, such as SV40, as known in the art.

In the recombinant vector, the sequence of the polynucleotide encoding the fusion protein may be operatively linked to a promoter. The term "operatively linked" used herein means a functional linkage between a nucleotide expression regulating sequence and other nucleotide sequences. Thus, the nucleotide expression regulating sequence may regulate the transcription and/or translation of the other nucleotide sequences.

The recombinant vector may be a vector for expression, which may stably express the fusion protein in a host cell. The vector for expression may be a vector commonly used in the art for expressing foreign protein in a plant, animal or microorganism. The recombinant vector may be constructed using various methods known in the art.

The recombinant vector may be constructed for use in prokaryotic or eukaryotic host cells. For example, when a prokaryotic cell is used as a host cell, the expression vector used generally includes a strong promoter capable of initiating transcription (for example, $p_L^\lambda$ promoter, trp promoter, lac promoter, tac promoter, T7 promoter), a ribosome binding site for initiating translation, and a transcription/translation termination sequence. When a eukaryotic cell is used as a host cell, the vector can include an origin of replication acting in the eukaryotic cell. The origin of replication can be, e.g., c f1 origin of replication, SV40 origin of replication, pMB1 origin of replication, adeno origin of replication, AAV origin of replication, or BBV origin of replication, but is not limited thereto. The promoter in an expression vector for a eukaryotic host cell may be a promoter derived from genomes of mammalian cells (for example, a metallothionein promoter) or a promoter derived from mammalian viruses (for example, an adenovirus late promoter, a vaccinia virus 7.5K promoter, a SV40 promoter, a cytomegalovirus promoter, and a tk promoter of HSV). The transcription termination sequence in an expression vector for a eukaryotic host cell may be, in general, a polyadenylation sequence.

According to an embodiment of the present invention, there is provided a cell including a polynucleotide encoding a fusion protein including the polypeptide that has an amino acid sequence represented by Formula I and that inhibits binding between a VEGF and a VEGFR; and an Fc region of an antibody.

According to an embodiment of the present invention, there is provided a cell including a polynucleotide encoding a fusion protein including a polypeptide that has one amino acid sequence selected from the group consisting of SEQ ID NOS: 6 through 23 and that inhibits binding between a VEGF and a VEGFR; and an Fc region of an antibody.

The encoded fusion protein may further include a linker that links the polypeptide to the Fc region of the antibody.

The cell may be transformed with the polynucleotide encoding the fusion protein or with the recombinant vector including the polynucleotide and a promoter operatively linked to the sequence of the polynucleotide.

In other words, the cell may include the sequence of the polynucleotide encoding a fusion protein on the genome of the host cell, or a recombinant vector with the polynucleotide sequence included therein.

A host cell that is capable of stably and consecutively cloning or expressing the recombinant vector may be any host cell known in the art. The prokaryotic cell may be *Bacillus* genus bacterial cell, such as *E. coli* JM109, *E. coli* BL21, *E. coli* RR1, *E. coli* LE392, *E. coli* B, *E. coli* X 1776, *E. coli* W3110, *Bacillus subtilis*, and *Bacillus thuringiensis*, intestinal bacteria, such as *Salmonella typhimurium* and *Serratia marcescens*, and various *Pseudomonas* species. A eukaryotic host cell, may be a yeast (*Saccharomyce cerevisiae*), an insect cell, a plant cell, or an animal cell, for example, a CHO (Chinese hamster ovary), W138, BHK, COS-7, 293, HepG2, 3T3, RIN, or a MDCK cell.

The polynucleotide or the recombinant vector including the same may be transferred into the host cell using a method known in the art. For example, when a prokaryotic cell is used as the host cell, the transfer may be performed using a $CaCl_2$ method or an electroporation method, and when a eukaryotic cell is used as the host cell, the transfer may be performed by microinjection, calcium phosphate precipitation, electroporation, liposome-mediated transfection, or gene bombardment, but is not limited thereto.

The transformed host cell may be selected using a phenotype expressed by a selectable marker by known methods in the art. For example, when the selectable marker is a specific antibiotic resistance gene, a transformant is cultured in a medium including the antibiotic, whereby the transformant may easily be selected.

According to an embodiment of the present invention, there is provided a method of preparing a fusion protein, the method including culturing a cell including a polynucleotide encoding a fusion protein including the polypeptide that has an amino acid sequence represented by Formula and that inhibits binding between a VEGF and a VEGFR; and an Fc region of an antibody; and collecting protein expressed from the culture.

According to an embodiment of the present invention, there is provided a method of preparing a fusion protein, the method including culturing a cell including a polynucleotide encoding a fusion protein including a polypeptide that has one amino acid sequence selected from the group consisting of SEQ ID NOS: 6 through 23 and that inhibits binding between a VEGF and a VEGFR; and an Fc region of an antibody; and collecting protein expressed from the culture.

The fusion protein may further include a linker that links the polypeptide to the Fc region of the antibody.

The transformed host cell may be cultured using various a known method in the art. For example, a transformed host cell with fusion protein expression under the control of the lacZ promoter can be inoculated into LB liquid medium including an appropriate antibiotic and cultured therein, and isopropyl β-D-1-thiogalactopyranoside (IPTG) can be added to the LB liquid medium to induce protein expression by the lacZ promoter at a time when the density of the cell reaches a certain level, After culturing the cells, protein expressed within the cell or secreted to the culture medium may be collected.

The protein expressed inside the cell or secreted into the medium may be obtained in a purified form by using one of various known purification methods in the art. Examples of purification methods include solubility fractionation by use of ammonium sulphate, size differential filtration, and various chromatography methods (performing separation according to size, charge, hydrophobicity or affinity). For example, if the fusion protein includes glutathione-S-transferase (GST), the protein may easily be obtained using a glutathione-binding resin column, and if the fusion protein includes a 6×His sequence, the protein may easily be obtained using a $Ni^{2+}$-NTA His-binding resin column.

According to an embodiment of the present invention, there is provided a composition for preventing or treating angiogenesis-related diseases or cancer. The composition includes a fusion protein including a polypeptide that has one amino acid sequence selected from the group consisting of the amino acid sequence represented by Formula I and amino add sequences of SEQ ID NOS: 6 through 23 and that inhibits binding between a VEGF and a VEGFR; and an Fc region of an antibody; and a pharmaceutically acceptable carrier. The fusion protein may be present in a therapeutically effective amount.

The fusion protein may further include a linker that links the polypeptide to the Fc region of the antibody.

The composition may be used to prevent or treat cancer. Examples of the cancer are carcinoma, lymphoma, blastoma, sarcoma, and leukemia. In particular, the cancer may be squamous cell carcinoma, small-cell lung cancer, non-small-cell lung cancer, adenocarcinoma of the lung, squamous cell carcinoma of the lung, peritoneal carcinoma, skin cancer, melanoma in the skin or eyeball, rectal cancer, cancer near the anus, esophagus cancer, small intestinal tumor, endocrine gland cancer, parathyroid cancer, adrenal cancer, soft-tissue sarcoma, urethral cancer, chronic or acute leukemia, lymphocytic lymphoma, hepatoma, gastrointestinal cancer, pancreatic cancer, glioblastoma, cervical cancer, ovarian cancer, liver cancer, bladder cancer, hepatocellular adenoma, breast cancer, colon cancer, large intestine cancer, endometrial carcinoma or uterine carcinoma, salivary gland tumor, kidney cancer, prostate cancer, vulvar cancer, thyroid cancer, or various types of head and neck cancers, but is not limited thereto.

In addition, the composition may be used to prevent or treat an angiogenesis-related disease. Angiogenesis is a physiological process involving the formation of new capillary vessels from existing vessels. If the angiogenesis is not regulated autonomously, the vessels are abnormally grown, causing diseases. Examples of the angiogenesis-related disease are rheumatoid arthritis, osteoarthritis, septic arthritis, psoriasis, corneal ulcer, age-related macular degeneration, diabetic renopathy, proliferative vitreoretinopathy, premature retinopathy, keratoconus, Sjogren's syndrome, myopia ocular tumors, corneal graft rejection, abnormal wound healing, bone diseases, proteinuria, abdominal aortic aneurysm diseases, degenerative cartilage loss due to traumatic joint damage, nervous system demyelination diseases, liver cirrhosis, glomerular disease, premature rupture of embryonic membranes, inflammatory bowel disease, periodontal disease, arteriosclerosis, restenosis, central nervous system inflammation diseases, Alzheimer's disease, skin aging, and cancer invasion and metastasis, but are not limited thereto.

The composition for preventing or treating angiogenesis-related diseases or cancers includes a pharmaceutically acceptable carrier. The pharmaceutically acceptable carrier, which is commonly used in formulation, may be lactose, dextrose, sucrose, sorbitol, mannitol, starch, gum acacia, calcium phosphate, alginates, gelatin, calcium silicate, microcrystalline cellulose, polyvinylpyrrolidone, cellulose, water, syrup, methyl cellulose, methylhydroxy benzoate, propylhydroxy benzoate, talc, magnesium stearate, and mineral oil, but is not limited thereto. The pharmaceutical composition may further include a lubricant, a wetting agent, a sweetener, a flavor enhancer, an emulsifying agent, a suspension agent, and a preservative.

The composition for preventing or treating an angiogenesis-related disease or cancer may be administered orally or parenterally. The parenteral administration may include intravenous injection, subcutaneous injection, muscular injection, intraperitoneal injection, endothelial administration, local administration, intranasal administration, intrapulmonary administration, and rectal administration. Since oral administration can lead to digestion of protein or peptide, the composition may be coated or the composition may be formulated to prevent the digestion. In addition, the composition may be administered by a device capable of transferring an active material to a target cell.

A suitable dose of the composition for preventing or treating an angiogenesis-related disease or cancer may depend on many factors, such as formulation methods, administration methods, ages of patients, body weight, gender, pathologic conditions, diets, administration time, administration route, excretion speed, and reaction sensitivity. A desirable dose of the composition may be in the range of about 0.001 to about 100 mg/kg for an adult. The term "therapeutically effective amount" used herein refers to a sufficient amount used in preventing or treating cancer or an angiogenesis-related disease.

The composition may be formulated using a pharmaceutically acceptable carrier and/or an additive by a known method in the art and prepared in a unit dose form or be contained in a multi-dose container. In this regard, the formulation may be a solution in oil or an aqueous medium, a suspension, a syrup, an emulsifying solution, an extract, powder, granules, a tablet, or a capsule, and may further include a dispersing or a stabilizing agent. In addition, the composition may be administered as an individual drug, or together with other drugs, and may be administered sequentially or simultaneously with other drugs.

According to an embodiment of the present invention, there is provided a method of treating an angiogenesis-related disease or cancer of an animal, the method including administering to a subject a therapeutically effective amount of a fusion protein including: a polypeptide that has one amino acid sequence selected from the group consisting of the amino acid sequence represented by Formula I and amino acid sequences of SEQ ID NOS: 6 through 23 and that inhibits binding between a VEGF and a VEGFR; and an Fc region of an antibody. The fusion protein can be in the form of a composition including a pharmaceutically acceptable carrier.

The fusion protein may further include a linker that links the polypeptide to the Fc region of the antibody.

A detailed description of the composition for preventing or treating an angiogenesis-related disease or cancer and the administration method thereof has already been provided above.

The subject to which the fusion protein is administered includes animals. For example, the animals may be humans, dogs, cats, or mice.

One or more embodiments of the present invention will now be described in further detail with reference to the following Examples. However, these examples are for the illustrative purposes only and are not intended to limit the scope of the invention.

EXAMPLE 1

Screening for Polypeptides Specifically Binding to VEGF

A process of screening for polypeptides specifically binding to VEGF is schematically illustrated in FIG. 1.

(1) Biopanning

A human VEGF (R&D systems, Inc.: catalog #293-VE) was immobilized on an appropriate solid surface (for example, a plate), a phage display polypeptide library (Dyax) was added thereto to be bound to the VEGF, and under various binding times and washing conditions, polypeptide expression phages binding to the VEGF with high binding affinity were selected.

The biopanning was performed by bead panning. In particular, magnetic beads with streptavidin attached to the bead surface and a VEGF with biotin bound thereto were mixed together, and then the mixture was stirred at 4° C. for 18 hours to immobilize the VEGF on the surface of the magnetic beads. The magnetic beads with the VEGF immobilized thereon were blocked with skim milk at room temperature for two hours, and then a polypeptide displaying phage solution was added to the magnetic beads. The mixture was stirred for reaction for two hours, and washed using a phosphate buffered saline (PBS) solution (1.06 mM $KH_2PO_4$, 155.17 mM NaCl, 2.97 mM $Na_2HPO_4$-$7H_2O$) and a PBS solution including 0.1% Tween-20. Then, the phages bound to the VEGF immobilized on the beads were separated from the solution. The biopanning process was performed up to two or three times.

(2) Phage ELISA and Determination of Sequences of Polynucleotides Encoding the Polypeptides Specifically Binding to Vegf and Sequences of the Polypeptides

*E. coli* XL1-Blue was infected with each of the phage clones obtained from the biopanning process, and the cells were cultured at 37° C. for 14 hours to obtain a phage solution. The VEGF was added to a 96-well microtiter plate (Nunc), and maintained at 4° C. for 18 hours to immobilize the VEGF on a surface of the plate. The plate with the immobilized VEGF was blocked with skim milk at room temperature for 1 hour, and 100 µl of the phage solution was added to the plate. Then, the phage and the VEGF were incubated together at room temperature for two hours, and washed using a PBS solution containing 0.1% Tween-20. Subsequently, an anti-M13 antibody (GE Healthcare) specifically reactive to the phage and conjugated with horseradish peroxidase (HRP) was added to the resultant product and incubated with each other at room temperature for 1 hour. Then, the plate was washed twice with a PBS solution containing 0.1% Tween-20. Lastly, 100 µl of trimethylbenzidine (TMB) (SIGMA), an HRP substrate, was added to each well of the plate to induce a color reaction. The reaction was stopped by adding 50 µl of 5N $H_2SO_4$ solution. The $OD_{450}$ value was read on a plate reader (Molecular Devices). From the results, a total of 23 phage clones were identified as having a high binding affinity with the VEGF. To determine the base sequence of polynucleotides encoding the polypeptides specifically binding to the VEGF obtained from single clones of the phages, a colony polymerase chain reaction (PCR) was performed using two different primer sets (primer set SEQ ID NOS: 47 and 48; and primer set SEQ ID NOS: 49 and 50). Each primer set was used according to the origin of the Dyax polypeptide library. For example, the primer set having SEQ ID NOS: 47 and 48 was used to confirm that the encoded number of amino acids of a polypeptide displayed in a phage is 8 or 9, and the primer set having SEQ ID NOS: 49 and 50 was used to confirm that the encoded number of amino acids of a polypeptide displayed in a phage is 10. The PCR was performed using a GeneAmp PCR system 9700 (Applied Biosystem), with the following PCR conditions: 30 cycles of 94° C. for 5 minutes, 94° C. for 1 minute, 60° C. for 1 minute, and 72° C. for 1.5 minutes; 72° C. for 10 minutes; and cooling to 4° C. Subsequently, polynucleotide fragments obtained by the PCR reaction were washed and then sequenced (Solgent). The amino acid sequence of a polypeptide specifically binding to the VEGF was determined from the nucleotide sequence of the polynucleotide encoding the polypeptide (refer to Table 1), Table 1 below shows the amino acid sequences of the region of the polypeptides displayed in the phage that specifically bind to the VEGF and the polynucleotide base sequences encoding the polypeptide regions.

A polynucleotide encoding the polypeptide obtained according to Example 1 was cloned into a vector expressing an Fc region of a human antibody. The vector used has a cytomegalovirus (CMV) promoter, and includes a polynucleotide encoding the Fc region of a human antibody. The polynucleotide encoding a polypeptide of Example 1 was cloned into the vector such that it was linked to the 3" end of the polynucleotide encoding the Fc region of the human antibody. Thus, in the expressed fusion protein, the polypeptide of Example 1 was linked to the C-terminal end of the polypeptide constituting the Fc region of the human antibody. In particular, the polynucleotide encoding a polypeptide of Example 1 and the vector were respectively digested with restriction enzymes, i.e., Not I (Roche) and Xba I (Roche), and the resultant products were ligated with each other by using a T4 DNA lagase (NEB) to prepare a vector for expressing a peptibody including the desired polypeptide region. The prepared recombinant vectors were transfected into HEK-293E cells distributed by the Korean Research Institute of Biotechnology. To express the fusion protein, the HEK-293E cells were cultured in serum-free Dulbecco's Modified Eagle Medium (DMEM) (Invitrogen), which was changed four times at intervals of three days. The resultant culture solution was centrifuged to remove residues and impurities included therein. The expressed fusion protein was purified from the centrifuged culture solution using protein A affinity chromatography column (AKTAexplorer, GE Healthcare). From the results, it was confirmed that the purified protein was the fusion protein in which a polypeptide shown in Table 1 was linked to an Fc region of a human antibody (refer to FIG. 2). FIG. 2 presents results of Coomassie blue-stained nondenatured and denatured polyacrylamide gel electrophoresis on several of the fusion proteins disclosed herein. In FIG. 2, the lane label SM means size marker, while 42, 46, 56, 70 refer to the polypeptide clone number of the sample. The bands are the fusion proteins. The gels confirmed that the fusion proteins were expressed with a correct molecular weight and had the expected conformation, since the location of bands in the non-denaturing gel were consistent with dimmers, whereas monomers were shown in the SDS PAGE gel.

TABLE 1

| Polypeptide clone number | Amino acid sequence | | Base sequence of polypeptide cDNA | |
|---|---|---|---|---|
| 55 | PRFEMWHDDK | (SEQ ID NO: 1) | cctcgttttgagatgtggcatgatgataag | (SEQ ID NO: 24) |
| 63 | PRLSMWQNME | (SEQ ID NO: 2) | cctcgtctttctatgtggcagaatatggag | (SEQ ID NO: 25) |
| 66 | DRFSMWKNLE | (SEQ ID NO: 3) | gatcgttttctatgtggaagaatcttgag | (SEQ ID NO: 26) |
| 70 | SRFEMWNDIS | (SEQ ID NO: 4) | tctcgttttgagatgtggaatgatatttct | (SEQ ID NO: 27) |
| 80 | DRFTMWDSQS | (SEQ ID NO: 5) | aatcgtcttattatgcatacttctgagcag | (SEQ ID NO: 28) |
| 50 | QRDQQYKHMY | (SEQ ID NO: 6) | cagcgtgatcagcagtataagcatatgtat | (SEQ ID NO: 29) |
| 16 | DRYSQYQSPM | (SEQ ID NO: 7) | gatcgttattctcagtatcagtctcctatg | (SEQ ID NO: 30) |
| 52 | DFLKMYRDEK | (SEQ ID NO: 8) | gattttcttaagatgtatcgtgatgagaag | (SEQ ID NO: 31) |
| 56 | MHRPWPWDMF | (SEQ ID NO: 9) | atgcatcgtccttggccttgggatatgttt | (SEQ ID NO: 32) |
| 65 | QMDRMFPHVG | (SEQ ID NO: 10) | cagatgggatcgtatgtttcctcatgttggt | (SEQ ID NO: 33) |
| 68 | PIGQRWNRLE | (SEQ ID NO: 11) | cctattggtcagcgttggaatcgtcttgag | (SEQ ID NO: 34) |
| 69 | RLFEMYPSLE | (SEQ ID NO: 12) | cgtcttttgagatgtatccttctcttgag | (SEQ ID NO: 35) |
| 73 | ERTEMFPSAS | (SEQ ID NO: 13) | gagcgtactgagatgtttccttctgcttct | (SEQ ID NO: 36) |
| 76 | QRDEMYPHLN | (SEQ ID NO: 14) | cagcgtgatgagatgtatcctccatcttaat | (SEQ ID NO: 37) |
| 78 | PHQEMWQFES | (SEQ ID NO: 15) | cctcatcaggagatgtggcagtttgagtct | (SEQ ID NO:38) |
| 82 | MKSAMYHDIR | (SEQ ID NO: 16) | atgaagtctgctatgtatcatgatattcgt | (SEQ ID NO: 39) |
| 83 | FDKYYRDWFI | (SEQ ID NO: 17) | tttgataagtattatcgtgattggtttatt | (SEQ ID NO: 40) |
| 40 | RMGPFGTTH | (SEQ ID NO: 18) | cgtatgggtccttttggtactactcat | (SEQ ID NO: 41) |
| 42 | YRGVWGGYF | (SEQ ID NO: 19) | tatcgtggtgtttggggtggttatttt | (SEQ ID NO: 42) |
| 44 | HDYAFYSAW | (SEQ ID NO: 20) | catgattatgcttttattctgcttgg | (SEQ ID NO: 43) |
| 13 | EDYRFYSVW | (SEQ ID NO: 21) | gaggattatcgttttattctgtttgg | (SEQ ID NO: 44) |
| 46 | TWWTHDFTI | (SEQ ID NO: 22) | actcgtcttcagattcttttggggtgtt | (SEQ ID NO: 45) |
| 34 | YGYPWSGT | (SEQ ID NO: 23) | tatggttatccttggtctggtact | (SEQ ID NO: 46) |

EXAMPLE 2

Determination of Fusion Protein Ability to Bind to VEGF

ELISA was used to confirm whether the fusion proteins prepared according to Example 1 recognized a VEGF. First, 50 μl (2 μl/ml) of a human VEGF (R&D System 50 μl (2 μg/ml) of a mouse VEGF (R&D Systems), or 50 μl PBS as a control were respectively added to each well of a plate to be bound on a surface of the plate, and the resultant product was washed to remove unreacted VEGF. Then, 50 ng of the isolated fusion protein of Example 1 was added to each well of the plate, and incubated for 1 hour. Subsequently, the resultant products were washed with a PBS solution including 0.05% Tween-20 to remove unreacted fusion protein. An anti-human Fc antibody (PIERCE) with horseradish peroxidase (HRP) bound thereto was added to each well of the plate, and incubated at room temperature for 30 minutes. Then, the resultant product was washed with a Tris-buffered saline Tween-20 (TBS-T) solution. Subsequently, a peroxidase substrate solution (o-phenylene diamine (OPD) solution) was added and the degree of reaction was evaluated by measuring the absorption at 450 nm using an ELISA reader. From the results, the ability of the fusion proteins of Example 1 to bind to the mouse or human VEGF was determined. The results are shown in FIGS. 3 and 4.

Figure 3:
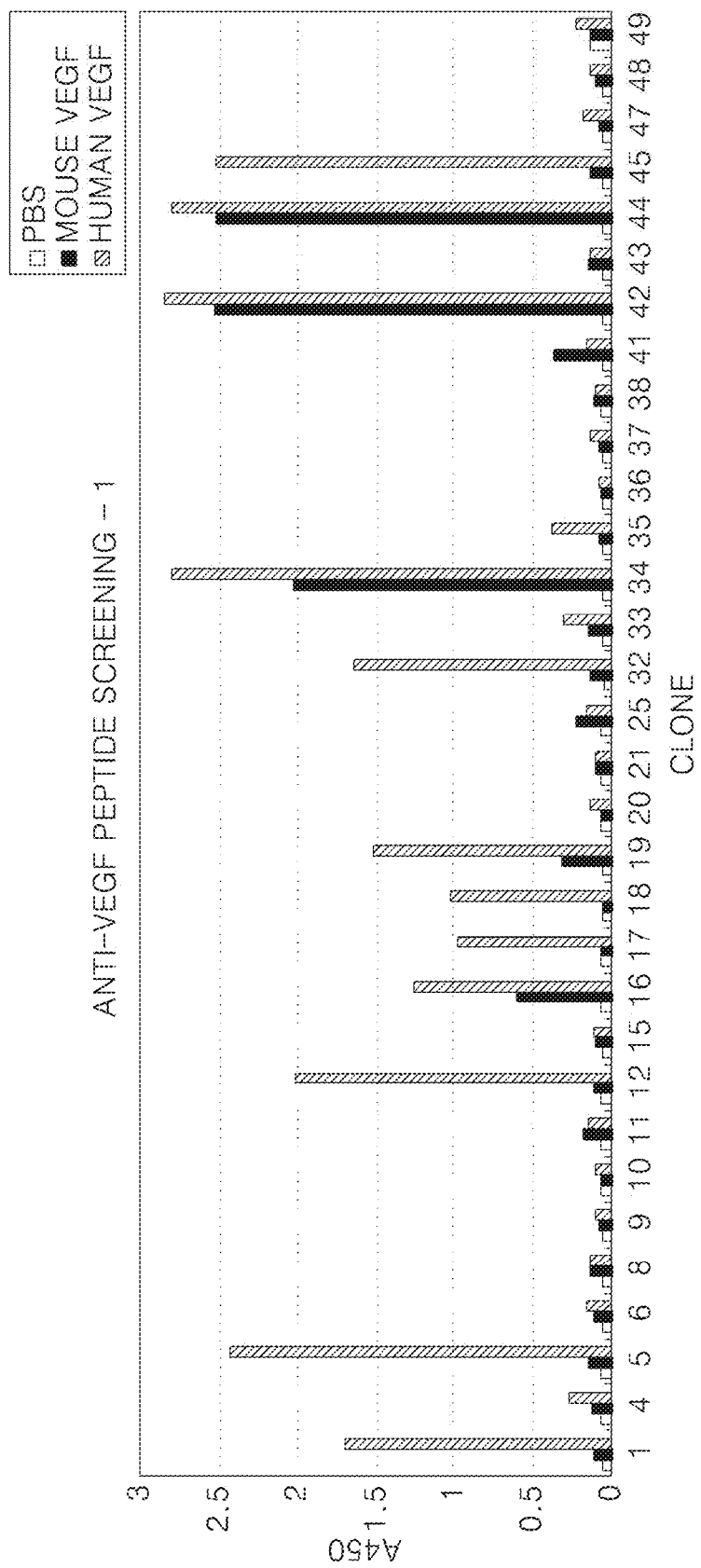
FIG. 3 is a histograph showing binding (measured as $A_{450}$) between various fusion proteins (designated by clone number) according to an embodiment of the present invention and mouse- or human-derived vascular endothelial growth factor.
Figure 4:
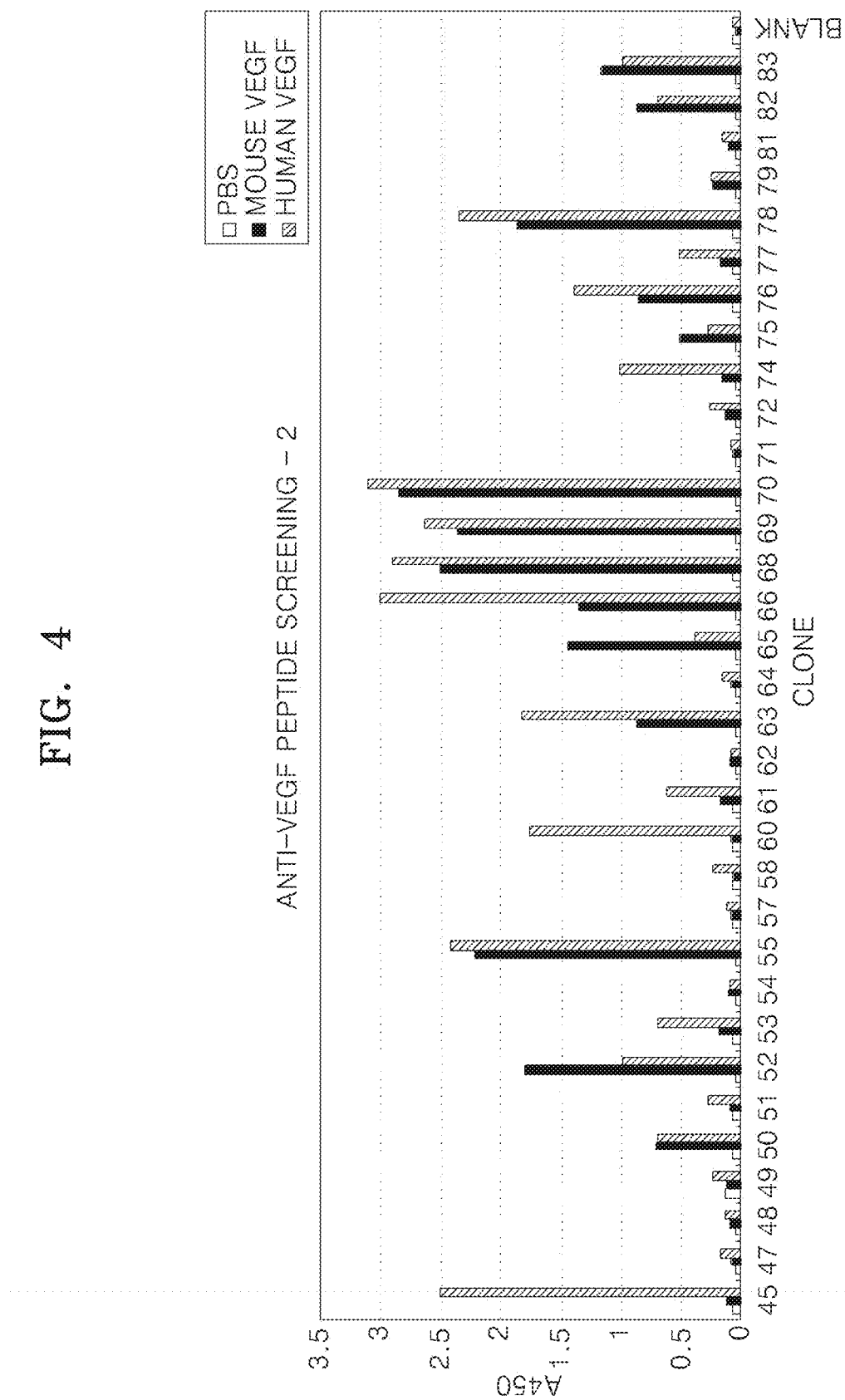
FIG. 4 is a histograph showing binding (measured as $A_{450}$) between various fusion proteins according to an embodiment of the present invention and a mouse- or human-derived vascular endothelial growth factor.

Referring to FIGS. 3 and 4, it is seen that many of the fusion proteins of Example 1 have a high binding affinity with a mouse- and/or human-derived VEGF.

EXAMPLE 3

Determination of Fusion Protein Ability to Inhibit Binding Between VEGF and VEGFR Competitive ELISA was used to evaluate the ability of the fusion proteins to inhibit binding between VEGF and VEGFR.

0.5 µl/ml of a mouse-derived VEGF (R&D Systems) was immobilized on a 96-well MaxiSorp™ flat-bottom plate (Nunc), the plate was washed with phosphate buffered saline (PBS) containing 0.1% Tween-20 five times, and then the plate was blocked with PBS containing 5% bovine serum albumin (BSA) at room temperature for 2 hours. Then, 100 of the isolated fusion proteins of Example 1 was added to wells of the plate at concentrations of 0.0625 µg/ml, 0.625 µg/ml, 6.25 µg/ml, 31.5 µg/ml, and 62.5 µg/ml, respectively. For comparison, the commercially available humanized monoclonal antibody AVASTIN (Genentech) that specifically recognizes and blocks VEGF was also added to wells of the plate at the same concentrations. The plate was incubated at room temperature for two hours. Subsequently, 1 µg/ml of a VEGFR(R&D Systems) was added to each well and the plate was incubated at room temperature for two hours. After the incubation was terminated, the plate was washed five times with PBS containing 0.1% Tween-20. A mouse anti-VEGFR antibody (R&D Systems) was diluted to 1:5,000 with PBS containing 1% BSA, added to the plate weds, and then the plate was incubated at room temperature for 1 hour. Then, 100 of goat anti-mouse-IgG-HRP (Pierce), diluted with PBS containing 1% BSA to a ratio of 1:5,000, was added to each well of the plate, incubated at room temperature for 30 minutes, and then washed five times with PBS containing 0.1% Tween-20. Lastly, 100 µl of trimethylbenzidine (TMB) (SIGMA) was added to each well of the plate to induce a color reaction, and the reaction was stopped by adding 50 µl of 5N $H_2SO_4$ solution. The $OD_{450}$ value was read on a plate reader (Molecular Devices). The results are shown in FIG. 5.

Figure 5:
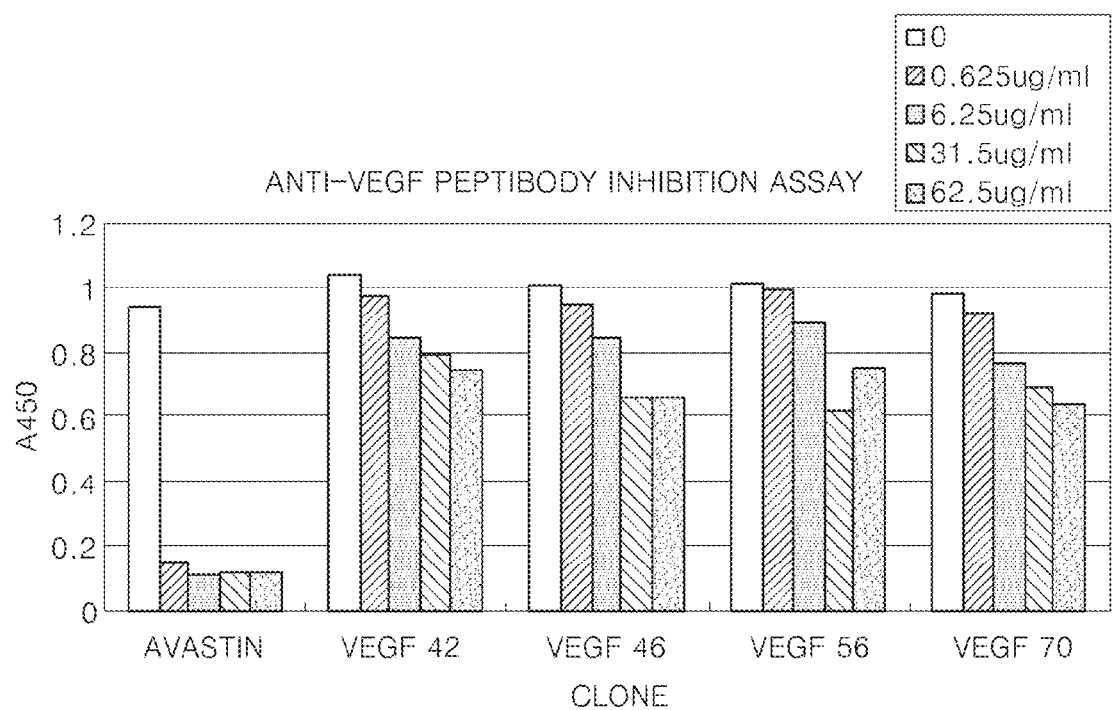
FIG. 5 is a histograph showing results of a competitive enzyme-linked immunosobent assay (ELISA) measuring ability of various fusion proteins according to an embodiment of the present invention and the commercially available drug AVASTIN to inhibit binding between a vascular endothelial growth factor and a vascular endothelial growth factor receptor.

Referring to FIG. 5, it is seen that the fusion proteins including a polypeptide shown in Table 1 has an excellent effect of inhibiting binding between a VEGF and a VEGFR. In addition, since the degree of inhibition depended on the amount of the fusion protein added to the sample, it was confirmed that the fusion protein inhibited the binding between the VEGF and the VEGFR.

As described above, according to one or more embodiments of the present invention, a polypeptide specifically binding to VEGF or specifically inhibiting VEGFR-VEGF binding or a fusion protein including the polypeptide may efficiently prevent or treat an angiogenesis-related disease or cancer.

The terminology used herein is for the purpose of describing particular embodiments only and is not intended to be limiting of the invention. The terms "a" and "an" do not denote a limitation of quantity, but rather denote the presence of at least one of the referenced item. The terms "comprising", "having", "including", and "containing" are to be construed as open-ended terms (i.e. meaning "including, but not limited to").

Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable.

All methods described herein can be performed in a suitable order unless otherwise indicated herein or otherwise clearly contradicted by context. No language in the specification should be construed as indicating any non-claimed element as essential to the practice of the invention as used herein.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. An isolated polypeptide consisting of the amino acid sequence of SEQ ID NO: 22.

2. The polypeptide of claim 1, wherein the polypeptide specifically binds to a vascular endothelial growth factor.

3. An isolated fusion protein comprising:
   (a) a polypeptide consisting of the amino acid sequence of SEQ ID NO: 22; and
   (b) an Fc region of an antibody.

4. The fusion protein of claim 3, further comprising a linker that links the polypeptide consisting of SEQ ID NO: 22 to the Fc region of the antibody.

5. The fusion protein of claim 3, wherein the Fc region of the antibody is derived from an animal selected from the group consisting of a human, a mouse, a rabbit, and a goat.

6. A method of preparing a fusion protein, the method comprising:

culturing a cell expressing the fusion protein of claim 3; and collecting fusion protein expressed from the culture.

* * * * *